United States Patent [19]

Rof

[11] Patent Number: 5,240,714
[45] Date of Patent: Aug. 31, 1993

[54] NON-DIGOXIN-LIKE NA+, K+-ATPASE INHIBITORY FACTOR

[76] Inventor: Jose M. S. Rof, Gavilanes, 1, Torre 3, 10-D, Madrid 28035, Spain

[21] Appl. No.: 399,908

[22] Filed: Aug. 29, 1989

[51] Int. Cl.$^5$ .................. A61K 35/12; A61K 39/30; A61K 35/55

[52] U.S. Cl. .................. 424/570; 424/520; 424/529; 424/531; 424/545; 424/562

[58] Field of Search ............... 424/520, 529, 531, 545, 424/562, 570

[56] References Cited

PUBLICATIONS

Morgan et al. Endocrinology vol. 115 No. 4 pp. 1642-1644 1984.
Haber et al. Hypertension vol. 9 No. 4 pp. 315-324 1987.
Yamador et al. Bioscience Reports vol. 3 pp. 947-954 1983.
Carilli et al. J. Biological Chemistry vol. 260 No. 2 pp. 1027-1031 1985.
Alaghband-Zadeh et al. J. Endocrinology vol. 98 pp. 221-226. 1983.
Faure. Klin Wochenschr vol. 65 (suppl vol. 111) pp. 49-52 1987.
Crabos et al. Amer. J. Physiol. vol. 23 F912-917 1988.
Haddy et al. Fed. Proc. vol. 44 No. 12 1985.
Article entitled: "Sodium transport inhibitor inhibitor from bovine hypothalamus"; by Garner T. Haupert, Jr. and JosE M. Sancho; Proc. Natl. Acad. Sci. USA, vol. 76, No. 9, pp. 4658-4660 Sep., 1979, Medical Sciences. Manuscript subsequently published in *Life Science Advances*, vol. 6, (1987), by M. Illescas, M. Ricote, E. Mendez and J. M. Sancho, Entitled: "Ouabain-Like Inhibitor Isolated from Bovine Hypothalamus".
Reprint of article entitled: Partial Purification of a sodium pump inhibitor from bovine adenohypothysis . . . ", by M. Illescas, M. Ricote, E. Mendez, R. G. Robles and J. M. Sancho: Clin. and Eper.—Theory and Practice, A10 (Suppl. 1), 301-307 (1988).
Manuscript subsequently published in *Progress in Drug Research 1*, vol. 34 231-260 (1990); by William J. Wechter and Elaine J. Benaksas, Entitled: "*Natriuretic Hormones*".
Reprint of article entitled: "Complete purification of two identical Na+-pump inhibitors isolated from bovine hypothalamus and hypophysis" by M. Illescas, N. Ricote, E. Mendez, R. G. Robles and Jose Sancho, Elsevier Science Publishers B. V. vol. 261, No. 2, 436-440 (Feb. 1990).
Tamura et al., "Isolation and Characterization of a Specific Endogenous Na, K -ATPase Inhibitor from Bovine Adrenal", American Chemical Society, vol. 27, No. 12, pp. 4244-4452, 1988.
Halperin et al., "Characterization of a Inhibitor of the Na+/K+Pump in Human Cerebrospinal Fluid", The Journal of Biological Chemistry, vol. 263, No. 2, pp. 646-650, 1988.
Hamlyn et al., "Digitalis-like Activity in Human Plasma", The Journal of Biological Chemistry, vol. 264, No. 13, pp. 7395-7404, 1989.
Schoner et al., "The 'endogenous cardiac glycoside'", Cardiac Glycosides, pp. 135-142, 1986.
Lichtstein et al., "Identification of a Ouabain-Like Compound in Toad Skin and Plasma as a Bufodienolide (List continued on next page.)

*Primary Examiner*—Douglas W. Robinson
*Assistant Examiner*—J. Williams
*Attorney, Agent, or Firm*—Poms, Smith, Lande & Rose

[57] ABSTRACT

A highly purified, Na+,K+-ATPase inhibitory factor is disclosed herein. The factor does not cross-react with anti-digoxin antibody and exhibits uniquely characteristic UV absorbance maxima at approximately 202-210 nm and at 274-280 nm. The inhibitory factor has a molecular weight of less than 1000 Daltons, is non-peptidic, non-lipidic, and loses activity following charring or alkaline hydrolysis. The factor is useful as a pharmaceutical composition in methods for treating essential hypertension, cardiac malfunction and in regulating angiogenesis and active sodium transport and other conditions. Methods for purifying the factor from tissue and fluid extracts are also disclosed.

7 Claims, 5 Drawing Sheets

PUBLICATIONS

Derivative", Life Sciences, vol. 38, pp. 1261–1270, 1986.

Goto et al., "Existence of a Polar Digitalis-Like Factor in Mammalian Hypothalamus", Academic Press, Inc., pp. 953–958, 1989.

English and Cantley, 37 Delta Endotoxin Is a Potent Inhibitor of the (Na,K)-ATPase", The Journal of Biological Chemistry", vol. 261, No. 3, pp. 1170–1173, 1986.

Shlevin, "(Na+-K+)-ATPase Inhibitors: Implications for New Drug Discovery", Drug Development Research 4:275-284. (1984).

Diamandis et al., "Digoxin Immunoreactivity in Cord and Maternal Serum and Placental Extracts. Partial Characterizatio of Immunoreactive Subtances by High-Performance Liquid Chromatography and Inhibition of Na+, K -ATPase", Clinical Biochemistry, vol. 18, Feb. 1985.

Erdmann et al., "Endogenous digitalis, cardiodigin and other regulators of the sodium pump", Cardiac Glycosides, pp. 143–155, 1986.

Millett et al., "Na-K-ATPase-inhibiting and glucose-6-phosphate dehydrogenase-stimulating activity of plasma and hypothalamus of the Okamoto spontaneously hypertensive rat", Journal of Endocrinology Ltd. pp. 69–73, 1986.

Cloix et al., "High Yield-Purification of Urinary Na+-Pump Inhibitor" Biochemical and Biophysical Research Communications, vol. 131, No. 3, pp. 1234–1240, 1985.

Cloix et al., "Endogenous Na+-Pump Inhibitor Extracted From Human Urine: Further Biochemical Studies", Gower Medical Publishing Ltd., pp. 352–354, 1986 (Journal of Hypertension, vol. 4 (suppl 6).

Shacoori et al., "Inhibition of (Na+, K+)'ATPase and Mg++-ATPase by a Lysosomotropic Drug: Perhexiline Maleate, Research Communications in Chemical Pathology and Pharmacology, vol. 59, No. 2, Feb. 1988.

Oishi et al., "Inhibition of Na,K-ATPase and Sodium Pump by Anticancer Ether Lipids and Protein Kinase C Inhibitors Et-18-OCH$_3$ and Bm 41.440" Biochemical and Biophysical Research Communications, vol. 157, No. 3, pp. 1000–1006, 1988.

Krekler et al., "A Na+, K+-ATPase inhibitor isolated from pig kidney", Cardiac Glycosides, pp. 165–169, 1986.

Morgan et al., "Characterization and Partial Purification of the Sodium-Potassium-ATPase Inhibitor Released from Cultured Rate Hypothalamic Cells", The Journal of Biological Chemistry, pp. 1–6, 1985.

Seda et al., "Inhibition of partially purified rat brain Na+, K+-dependent ATPase by bile acids, phenolic acids and endotoxin", Clinical Science (1984) 66, pp. 415–420.

Toseland et al., "Tentative Identification of a Digoxin-like Immunoreactive Substance", Therapeutic Drug Monitoring, vol. 10, pp. 168–171, 1988.

Haupert et al., "Hypothalamic sodium-transport inhibitor is a high-a-finity reversible inhibitor of Na+-K+ATPase, American Physiological Society, pp. 919–92, 1984.

Kelly et al., "Identification of NaK-ATPase Inhibitors in Human Plasma as Nonesterified Fatty Acids and Lysophospholipids", pp. 11704–11711, 1986.

Haber and Haupert, Jr., "The Search for Hypothalamic Na+, K+-ATPase Inhibitor", Hypertension, vol. 9, No. 4, pp. 315–324, Apr. 1982.

Tamura et al., "Na+, K+-ATPase Inhibitors from Acute Volume-expanded Hog Plasma", pp. 9672–9677, 1986.

Clarkson and de Wardener, "Observations on a Low Molecular Weight Natriuretic and Na-K-ATPase Inhibitory Material in Urine", Clin. and Exper.-Theory and Practice, A7(5&6), 673–683 (1985).

Lichtstein and Samuelov, "Endogenous 'Quabain Like-'Activity in Rat Brain", Biochemical and Biophysical Research Communications, vol. 96, No. 4, pp. 1518–1523, 1980.

MOrgan and Mir, "A passive sodium transport inhibitory factor (inhibitin) released from leukaemic promyelocytes in culture", Clinical Science (1984) 66, pp. 365–368.

Morgan et al., "Release of an Active Sodium Transport Inhibitor (ASTI) from Rat Hypothalamic Cells in Culture", Endoerinology, vol. 115, No. 4, pp. 1642–1645, 1984.

Fagoo and Godfraind, "Further characterization of cardiodigin, Na+, K+-ATPase inhibitor extracted from mammalian tissues", Febs Letters, vol. 184, No. 1, pp. 2540–2544, 1985.

Graves and Williams, "Endogenous Digitalis-Like Natriuretic Factors", Ann. Rev. Med. 1987, 38:, pp. 433–444.

Morgan et al., "Characterization and Partial Purification of the Sodium-Pota ATPase Inhibitor Released from Cultured Rat Hypothalamic", The Journal of Biological Chemistry, vol. 280, No. 25, pp. 13595–13600, 1985.

Graves and Williams, "An Endogenous Ouabain-Like Factor Associated with Hypertensive Pregnant Women", Journal of Clinical Endoerinology and Metalolism, vol. 59, No. 4, pp. 1070–1074, 1984.

Akaqawa et al., "Partial Purification and Properties of the Inhibitors of Na,K-ATPase and Ouabain-Binding in Bovine Central Nervous System", Journal of Neurochemistry, pp. 775–780, 1984.

Wechter, Table Two "Putative Natriuretic Hormones", Mar. 5, 1991, pp. 1–4.

and also demonstrated that plasma extract from saline-
NON-DIGOXIN-LIKE NA+, K+-ATPASE INHIBITORY FACTOR

FIELD OF THE INVENTION

The present invention is directed to a highly purified non-digoxin-like Na+, K+-ATPase inhibitory factor having utility as a therapeutic treatment for essential hypertension and cardiac malfunction as well as for regulating angiogenesis, cation transport, sodium excretion and other conditions in mammals. The present invention is also related to the isolation, purification, identification and characterization of this inhibitory factor from mammalian tissue and fluid sources.

BACKGROUND OF THE INVENTION

Over the past two decades numerous investigators have devoted significant effort to the study of partially purified extracts of mammalian tissue and fluids in order to identify and confirm the existence of endogenous humoral factors that may be involved in the regulation of cation transport in tissues as well as in the regulation of sodium excretion. At present, considerable evidence has been produced supporting the existence of such an endogenous factor or family of factors that is believed to inhibit the Na+, K+-ATPase enzyme system which regulates active sodium transport. Moreover, these inhibitory properties implicate the involvement of such factors in several physiological roles including natriuresis, the excretion of abnormal amounts of sodium in the urine, as well as in the genesis of certain forms of hypertension and cardiac malfunction.

However, in spite of the extensive data produced by these early investigators, considerable controversy exists with respect to the identity and characterization of such endogenous factors as well as with respect to their mechanisms of action. It is believed that the primary reason for this controversy may be due to the fact that these early investigators often obtained conflicting and contradictory results due to their inability to effectively purify the tissue and fluid extracts utilized in their studies. A consequence of this reported disparity in described characteristics has been to suggest that the inhibitory factors identified and studied in the prior art may be of more than a single type or, possibly, may be a variety of relatively low potency substances producing non-specific inhibition.

The early research in this field initially suggested that an endogenous humoral factor, or factors, may have been involved in regulating cation transport in vital tissues as well as in the regulation of sodium excretion by the kidney. Such factors were also indicated as being active in regulating vascular reactivity in arterioles. More specifically, these early studies demonstrated in dogs that an infusion of saline produced a rise in urinary sodium excretion even when the glomerular filtration rate and renal blood flow were reduced. See, de Wardener, H. E., et al., "Studies On The Efferent Mechanism Of The Sodium Diuresis Witch Follows The Administration Of Intravenous Saline In The Dog." Clin Sci. 1961;21:249-258. That a humoral factor was involved in regulating sodium transport was also indicated by the research of Dahl, L. K., et al., "Humoral Transmission Of Hypertension: Evidence From Parabiosis." Cir Res. 1969;24 (suppl 1): 21-23 where a salt-resistant rat was placed in parabiosis with a salt-sensitive rat and hypertension developed in the resistant rat when both animals were fed salt. Thus, under these conditions, it was presumed that a humoral hypertensive agent passed from the salt-sensitive rat to the salt-resistant rat.

Later research confirmed these preliminary results and also demonstrated that plasma extract from saline-loaded and volume-expanded dogs exhibited natriuretic, pressor, vascular sensitizing, and digoxin-like activities. See, Knock, C. A., et al. "Evidence In Vivo For A Circulating Natriuretic Substance In Rats After Expanding The Blood Volume." Clin Sci. 1980;59:411-421; Sonnenburg, H., et al., "A Humoral Component Of The Natriuretic Mechanism In Sustained Blood Volume Expansion." J Clin Invest. 1972;51:1631-1634 Knock, C. A., "Further Evidence In Vivo For A Circulating Natriuretic Substance After Expanding The Blood Volume In Rats." Clin Sci. 1980;59:423433; Pearce, J. W., et al., "Time Course Of Onset And Decay On Humoral Natriuretic Activity In The Rat." Can J Physiol Pharmacol. 1975;53:734-741; Bergele, A. H., et al., "Development Of Renal Response To Blood Volume Expansion In the Rat." Am J Physiol. 1974;227:364-368; Krecek, J., et al., "Sensitivity Of Prepubertal Rats To The Hypertensiogenic Effect Of Salt-A Lack Of Natriuretic Factor." In: Lichardus, B., et al., "Hormonal Regulation Of Sodium Excretion." Amsterdam: Elsevier North-Holland; 1980:289-297; Haddy, F. J., et al., "The Role Of Humoral Factors In Volume Expanded Hypertension." Life Sci. 1976;19:935-948; Gonick, H. C., et al., "Circulating Inhibitor Of Sodium-Potassium Activated Adenosine Triphosphatase After Expansion Of Extracellular Fluid Volume Rats." Clin Sci Mol Med. 1977;53:329-334.

Subsequent research provided evidence that a common humoral factor may be responsible for inhibition of Na+, K+-ATPase and sodium transport. For example, numerous studies have supported the proposition that the inhibition of Na+, K+-ATPase in the smooth muscle of the arteriole increases intracellular sodium, which increases intracellular calcium concentration and, as a result, the arteriolar tone. See, Blaustein, M. P., "Sodium, Ions, Calcium Ions, Blood Pressure Regulation And Hypertension: A Reassessment And A Hypothesis." Am J Physiol. 1977;232:C165-C173; Overbeck, H. W., et al., "Depressed Function Of A Ouabain-Sensitive Sodium-Potassium Pump In Blood Vessels From Renal Hypertensive Dogs." Circ Res. 1976;38(suppl 2):48-52; Pamnani, M., et al., "Demonstration Of A Humoral Inhibitor Of The (Na,K) Pump In Some Models Of Experimental Hypertension." Hypertension 1981;3,No. 6.:96-101; Pamnani, J. B., et al., "Vascular Sodium-Potassium Pump Activity In Various Models Of Experimental Hypertension." Clin Sci. 1980;59:-179 S-181 S; Hamlyn, J. M., et al. "A Circulating Inhibitor Of (Na,K)ATPase Associated With Essential Hypertension." Nature. 1982;300:650652; Poston, L., et al., "Evidence For A Circulating Sodium Transport Inhibitor In Essential Hypertension." Br Med J. 1981;282:1267-1269; MacGregor, G. A., et al., "Evidence For A Raised Concentration Of A Circulating Sodium Transport Inhibitor In Essential Hypertension." Br Med J. 1981;283:1355-1357; Devynck, M. A., et al., "Circulating Digitalis-Like Compounds In Essential Hypertension." Clin Exp Hypert. 1984;6:441-453.

Moreover, these studies also indicated that the factor or factors possessing these properties could function as an endogenous diuretic as well as be involved in certain forms of hypertension. For example, Poston, et al. demonstrated that normal leukocytes had low active sodium eflux and high intracellular sodium concentrations following incubation with the plasma of patients having essential hypertension. Similarly, Hamlyn, et al., MacGregor, et al., and Devynck, et al. showed that plasma from hypertensive patients contained a factor or factors that inhibited $Na^+$, $K^+$-ATPase.

Additional studies also supported the clear implication that such inhibitory factors are involved in the pathogenesis of hypertension. For example, the presence of a digoxin-like immunoreactive substance was demonstrated in the amniotic fluid of hypertensive pregnant women and in the plasma of preeclamptic pregnant patients. See. Graves, S. W., et al., "An Endogenous Ouabain-Like Factor Associated With Hypertensive Pregnant Women." *J Clin Endocr Matab.* 1984;59:1070-1075; Gudson, J. O., et al. "A Digoxin-Like Immunoreactive Substance In Preeclampsia." *Am J Obstet Gynecol.* 1984;150:83-85. However, as with the previously discussed research, the identity and characterization of the factor or factors in question remained obscure.

More recent research has been directed at attempting to identify the source of these suspected inhibitory factors. Several investigators have attempted to isolate such factors from brain extract and digitalis-like activity was reported in brain extract after various purification steps. See, Fishman, M.D., "Endogenous Digitalis-Like Activity In Mammalian Brain." *Proc Natl Acad Sci.* 1979;76.No.9.:4661-4663; Lichtstein, D., et al. "Endogenous Ouabain-Like Activity In Rat Brain." *Biochem Biophys Res Comm.* 1980;96,No.4:1518-1523. Similarly, it has been reported that a lesion in the anterioventral third ventricle in the volume-expanded rat decreased the level of $Na^+$, $K^+$-ATPase inhibition. See, Pamnani, M., et al. "Demonstration Of A Humoral Inhibitor Of The (Na,K) Pump In Some Models Of Experimental Hypertension." *Hypertension* 1981;3,No.6.:96-101; Pamnani, M., et al., "Vascular $Na^+$-$K^+$ Pump Activity In 'Acutely Saline-Loaded Rats With Anterioventral Third Ventricle (AV3V) Lesions [Abstract]." *Fed Proc.* 1981;40-390.

Additional research has focussed on more specific brain tissue sources. For example, extracts of bovine hypothalamus were reported by the present inventor to contain a factor that reduced sodium transport across anural membranes and also inhibited canine renal $Na^+$, $K^+$-ATPase. See, Haupert G. T., et al. "Sodium Transport Inhibitor From Bovine Hypothalamus." *Proc Natl Acad Sci.* 1979;76:4658-4660. However, these extracts were only partially purified and failed to characterize or identify the specific factor. Inhibitory activity has also been reported in extracts of rat hypothalamus and in cultures of hypothalamic neurons as well as from bovine adrenal tissues. See, Alaghband-Zadeh, et al., "Evidence That The Hypothalamus May Be A Source Of A Circulating $Na^+$-$K^+$-ATPase Inhibitor." *J Endocrinol.* 1983;98:221-226; Morgan, K., et al., "Release Of An Active Sodium Transport Inhibitor (ASTI) From Rat Hypothalamic Cells In Culture." *Endocrinol.* 1984;115,No.4:1642-1644; Tamura, M., et al. "Isolation and Characterization Of A Specific Endogenous $Na^+$,$K^+$-ATPase Inhibitor From Bovine Adrenal." *Biochemistry.* 988;27:4244-4253.

Other tissue and fluid extracts have also been examined. Plasma and urine extracts from volume expanded animals and humans have been reported to exhibit a natriuretic effect in over 25 separate studies as reviewed by de Wardener and Clarkson. See, de Wardener, H. E., et al., "Concept Of Natriuretic Hormone." *Physiol Rev.* 1985;65,No.3:658-759. Additionally, three fractions have been extracted from normal plasma which exhibit $Na^+$, $K^+$-ATPase inhibitory activity. See, Kelly, R. A., et al., "Characterization Of Digitalis-Like Factors In Human Plasma." *J Biol Chem.* 1985;260 no.21:113-96-11405. These fractions are also reported to cross react with digoxin antibodies.

Similar digoxin-like activity, such as cross-reaction with anti-digoxin antibodies, has been reported in deproteinized normal serum and urine. See. Balzan, S., et al., "Digoxin-Like Immunoreactivity In Normal Human Plasma And Urine, As Detected By A Solid-Phase Radioimmunoassay." *Clin Chem.* 1984;30:450-451; Cloix, J. F., et al. "High Yield-Purification Of A Urinary Na-Pump Inhibitor." *Biochem Biophys Res Comm.* 1985;131:1234-1240. Cloix, et al. believe that their digoxin-like sodium transport inhibitor is an amino-glyco steroid.

One group of investigators has partially isolated a sodium pump inhibitor from a variety of animal tissues utilizing reverse phase HPLC. See, Fagoo, M., et al., "Further Characterization Of Cardiodigin,$Na^+$-$K^+$-ATPase Inhibitor Extracted From Mammalian Tissues." *Febs Letters.* 1985;184:1631-1634. Evidencing some of the confusion regarding the characterization of such compounds, they have designated this inhibitor "cardiodigin" and believe it to be one of the recently identified lignan compounds found in mammalian fluids. Lignans are known to have several structural similarities to cardiac glycosides including a gamma butyrolactone ring which is deemed necessary for interaction with $Na^+$, $K^+$-ATPase. See, Fagoo, M., et al., "Evidence That Mammalian Lignans Show Endogenous Digitalis-Like Activities." *Biochim Biophys Acta.* 1986;134 n.4:1064-1070.

Further contributing to the confusion regarding the identify of these compounds, other endogenous molecules have also been implicated in $Na^+$, $K^+$-ATPase inhibition. These include the free fatty acids and ascorbic acid. Like the lignans, ascorbic acid also possesses a gamma butyrolactone ring and inhibits $Na^+$, $K^+$-ATPase. See. Ng, I., et al. "Ascorbic Acid: An Endogenous Inhibitor Of Isolated $Na^+$-$K^+$-ATPase." *Biochem Pharmacol.* 1985;34:2525-2530. However, ascorbic acid does not affect sodium transport in cells and therefore may not be a physiological regulator of sodium transport. Conversely, the free fatty acids have been implicated as endogenous regulators of sodium transport and have also been demonstrated to inhibit $Na^+$, $K^+$-ATPase. See, Bidard, J. N., et al. "A Search For An Ouabain-Like Substance From The Electric Organ Of Electrophorus Electricus With Led to Arachidonic Acid and Related Fatty Acids." *Biochem Biophys Res Comm.* 1984;-Actas 769:245-252; Tamura, M., et al. "Identification Of Linoleic And Oleic Acids As Endogenous $Na^+$-$K^+$-ATPase Inhibitors From Acute Volume-expanded Hog Plasma. (Abs.)." *J Biol Chem.* 1985;260:9672-9677. In this research by Tamura, et al. it was shown that the plasma of acutely volume-expanded pigs exhibited inhibitory activity and digoxin-like activity. Most of the reported activity was accounted for by an increase in linoleic acid and oleic acid, suggesting that free fatty acids regulate sodium excretion in acute volume expansion through depression of tubular sodium reabsorption. However, involvement of free fatty acids in the regulation of sodium excretion in normal physiological circumstances remains unknown.

As evidenced by the foregoing, in spite of the extensive research in this field, little agreement exists among the various investigators regarding the origin and character of such sodium transport inhibitory factors. In addition to the free fatty acids, lignans and other compounds previously discussed, some investigators have suggested that the factor or factors may be steroidal in view of the many similarities between the endogenous sodium transport inhibitor and digitalis. See. Cloix, et al. "High Yield-Purification Of A Urinary Na-Pump Inhibitor." *Biochem Biophys Res Comm* 1985;131:1234–1240; LaBella, F. S., et al. "Progesterone Derivatives That Bind To The Digitalis Receptor: Effects On Na+-K+-ATPase And Isolated Tissues." *Fed Proc.* 1985;44:2806–2828.

Conversely, other investigators have also identified the factor as a peptide. See, Kramer, H. J., et al. "Further Characterization Of The Endogenous Natriuretic And Digoxin-Like Immunoreacting Activities In Human Urine: Effects Of Changes In Sodium Intake." *Renal Physiol.* 1985;8:80–89. Similarly, two of the investigators using the hypothalamus as their tissue source have also presented evidence that the extracted factor or factors is a peptide. See. Morgan, K., et al. "Characterization And Partial Purification Of the (Na,K)ATPase Inhibitor Released From Cultured Rat Hypothalamic Cells." *J Bio Chem.* 1985;25:13595–13600; Akagawa, K., et al. "Partial Purification And Properties Of The Inhibitors Of Na,K-ATPase And Ouabain-binding In Bovine Central Nervous System." *J Neurochem.* 1984;42:775–780.

However, other researchers utilizing hypothalamic tissue sources have identified partially purified factor extracts which exhibit non-peptidic characteristics such as resistance to boiling hydrochloric acid. See, Haupert, G. T., et al. "Hypothalamic Sodium-Transport Inhibitor Is A High-Affinity Reversible Inhibitor Of (Na,K-)ATPase." *Am J Physiol.* 1984;247:F919–F924; Illescas, M., et al. "Partial Purification Of A Sodium Pump Inhibitor From Bovine Adenohypophysis. Its Comparison With The Natriuretic Factor Isolated From Hypothalamus." *J Clin Exp Hypertension.* 1988;A10:In press; Millett, J. A., et al. "Extraction And Characterization Of A Cytochemically Assayable Na/K-ATPase Inhibitor/Glucose-6-Phosphate Dehydrogenase Stimulator In The Hypothalamus And Plasma Of Man And The Rat." *J Endocr.* 1987;112:299–303.

Further compounding matters, two investigators utilizing plasma as their source of endogenous digitalis-like factors characterized their inhibitors as unsaturated fatty acids. See, Tamura, M., et al. "Identification Of Linoleic And Oleic Acids As Endogenous Na+-K+-ATPase Inhibitors From Acute Volume-expanded Hog Plasma. (Abs.)." *J Biol Chem.* 1985;260:9672–9677; Kelly, R. A., et al. "Identification Of NaK-ATPase Inhibitors In Human Plasma As Nonesterified Fatty Acids And Lysophospholipids." *J Biol Chem.* 1986;261 no.25:11704–11711.

In spite of the confusion regarding the identity and character of these compounds, that such endogenous sodium transport inhibitory factors may be implicated in several areas of human pathology has been established. Research has demonstrated that serum or urine from patients having essential hypertension contains sodium pump inhibitors. These inhibitory factors exhibit a variety of activities including inhibition of cellular active sodium fluxes, inhibition of Na+, K+-ATPase, positive entropy of the heart, increase in the pressor response to noradrenaline, competition with radio-labelled cardiac glycosides for binding sites (typically $^3H$ ouabain binding) as well as competition with radio-labelled antibodies raised against a cardiac glycoside.

It should be noted that the cardiac glycoside radioimmunoassay is the least reliable method for the detection of a sodium pump inhibitory factor because some compounds nonspecifically bind to common steroids such as aldosterone. See, Schreiber, V., et al. "Digoxin-Like Immunoreactivity Of Certain Steroid And Other Hormones." *Physiol Biochem.* 1981;30:569–571.

Numerous investigators have also shown that serum from patients with essential hypertension inhibits active sodium transport in normal leukocytes and lymphocytes. See, Oh, V., et al. "Reversible Inhibition Of Leucocyte Sodium Pumps By A Circulating Serum Factor In Essential Hypertension." *Bri Med J.* 1986;292:1551–1555; Gray, H. H., et al. "Effect Of Serum From Patient With Essential Hypertension On Sodium Transport In Normal Leukocytes." *Clin Sci.* 1986; 70:583–586; Moreth, K., et al. "Blood Pressure In Essential Hypertension Correlates With The Concentration Of A Circulating Inhibitor Of The Sodium Pump." *Klin Wochens.* 1986;64:239–244.

Poston, et al. incubated mixed, normal leukocytes with sera obtained from patents with essential hypertension and found that the depression of active sodium transport in the normal cells was equivalent to that in the cells of the patients. See, Poston, L., et al. "Evidence For A Circulating Sodium Transport Inhibitor In Essential Hypertension." *Br Med J.* 1981;282:1267–1269. Similarly, both Gray, et al. and Moreth, et al. found that the degree of abnormality conferred upon the normal cells correlated with the blood pressure of the patients from whom sera were obtained. Additionally, Oh and Taylor reported that incubation of serum from patients with essential hypertension with normal lymphocytes reduced the binding of radiolabeled ouabain in the cells.

Such results suggest the presence of a cardiac glucoside-like substance in the serum. Conversely, further contributing to the disparity of reported characteristics of such inhibitory factors, Boon, et al. could not demonstrate any effect of hypertensive serum on normal glucoside $^3H$ ouabain binding after incubation. See, Boon, et al. "Cation Transport Functions In Vitro In Patients With Untreated Essential Hypertension: A Comparison Of Erythrocytes And Leukocytes." *Clin Sci.* 1985;68:511–515.

It should be appreciated that at present there is no work clearly suggesting that erythrocyte sodium fluxes are affected by a sodium pump inhibitor in essential hypertension. Poston, et al. failed to demonstrate any inhibitory effect of hypertensive serum on normal erythrocytes although the sodium content of the patients' cells was high. Similarly, Millar, et al. found high erythrocyte sodium in their patient group yet were unable to demonstrate any effect of their patients' serum on normal erythrocytes. Millar, J. A., et al. "Evidence Against A Circulating Ouabain-Like Transport Inhibitor As A Cause Of Increased Red Cell Sodium In Essential Hypertension." *J Hipert.* 1984;2:461–463.

However, inhibition of $^3H$ ouabain binding after incubation of normal erythrocytes with a plasma extract from essential hypertension patients has been demonstrated. Cloix, et al. "Plasma Endogenous Sodium Pump Inhibitor In Essential Hypertension." *J Hypert.* 1983;1:11–14. However, though this inhibition correlated with the rate of urinary sodium excretion it did not correlate with blood pressure.

In spite of the foregoing, research has suggested that serum from patients with essential hypertension has cardiac glucoside-like properties and strongly supports a link between cellular sodium transport and venous tone in essential hypertension. For example, serum from patients with essential hypertension sensitizes the vascular response to catecholamines in a manner similar to the cardiac glycosides. Rabbit aortic strips incubated with plasma from patients with essential hypertension and subsequently stimulated with nonadrenaline produced a greater contraction than that evidenced in aortic strips exposed to normal plasma. See, Michelakis, A. M., et al. "Further Studies On The Existence Of A Sensitizing Factor To Pressor Agents in Hypertension." *J Clin Endocr Metab.* 1975;41:90–96.

Additionally, studies have directly demonstrated the inhibition of $Na^+$, $K^+$-ATPase by serum from patients with essential hypertension. For example, deproteinized plasma from normotensive and hypertensive subjects was tested on $Na^+$, $K^+$-ATPase isolated from dog kidney. The hypertensive plasma inhibited the enzyme to a degree correlated with the mean arterial pressure of the subject. See. Hamlyn, J. M., et al. "A circulating Inhibitor Of (Na,K)ATPase Associated With Essential Hypertension." *Nature.* 1982;300;650652. Similarly, it has been reported that plasma extract which inhibited $^3H$ ouabain binding in erythrocytes also inhibited dog kidney $Na^+$, $K^+$-ATPase activity. See, Cloix, J. F., et al. "Plasma Endogenous Sodium Pump Inhibitor In Essential Hypertension." *J Hypert.* 1983;1:11–14.

Indirect evidence of the existence of a sodium pump inhibitor in the serum of patients with essential hypertension has also been found in a cytochemical assay for the enzyme glucose 6-phosphate dehydrogenase (G6PDH). For example, G6PDH in guinea pig kidney cortical slices is stimulated by the inhibition of $Na^+$, $K^+$-ATPase. Accordingly, the degree of G6PDH stimulation by serum is an index of the serum $Na^+$, $K^+$-ATPase inhibitory activity. Moreover, serum from patients with essential hypertension stimulates cortical G6PDH to a degree correlating with the diastolic blood pressure of the patients. See, MacGregor, G. A., et al., "Evidence For A Raised Concentration Of A Circulating Sodium Transport Inhibitor In Essential Hypertension." *Br Med J.* 1981;283:1355–1357.

There are also reports evidencing an endogenous digoxin-like activity in serum from patients with essential hypertension. See, Fett, J. W., et al. "Isolation And Characterization Of Angiogenin And Angiogenic Protein From Human Carcinoma Cells." *Biochem.* 1985;24:5840. Fractionation studies of the concentrated deproteinized serum utilizing gel filtration suggests that several substances may be involved in this activity.

In spite of this evidence confirming that sodium transport is abnormal in essential hypertension patients and that this abnormality is due to a circulating sodium pump inhibitory factor or factors, whether such factors are involved in the genesis of essential hypertension remains to be conclusively proven. Moreover, the relationship of the previously discussed inhibitory factors to essential hypertension also remains to be conclusively proven.

Some researchers have suggested that essential hypertension is associated with a $Na^+$, $K^+$-ATPase inhibitory factor or factors which may account for abnormalities of the sodium pump. See, Haddy, F. J., et al. "Role Of A Humoral Sodium-Potassium Pump Inhibitor In Experimental Low Renin Hypertension." *Life Sci.* 19:30:571–575; de Wardener, H. E., et al. "Dahl's Hypothesis That A Saluretic Substance May Be Responsible For A Sustained Rise In Arterial Pressure: Its Possible Role In Essential Hypertension." *Kidney Int.* 1980;18:1–9. These reporters also suggest that this concept explains the effects of dietary sodium intake in hypertension. See, Houston, M. C. "Sodium And Hypertension." *Arch Intern Med.* 1986;146:179–185.

These same researchers propose an underlying, genetically determined kidney defect resulting in inadequate sodium excretion on a high salt intake and subsequent expansion of the ECFV. It is believed that this underlying defect may be an abnormality of sodium hydrogen exchange. See. Mahnensmith, R. L., et al. "The Plasma Membrane Sodium-Hydrogen Exchanger And Its Role In Physiological And Pathophysiological Processes." *Circ Res.* 1985;57:773–788.

Though there is uncertainty regarding the connection between sodium pump inhibitory factors and essential hypertension, it is clear that volume expansion leads to a production of a circulating sodium pump inhibitory factor or factors. By reducing renal tubular sodium reabsorption such factors could lead to a correction of the ECFV. Further, inhibition of sodium transport in vascular smooth muscle cells could also lead to a rise in their calcium content which would produce vasoconstriction and resultant high blood pressure. See, Blaustein, M. P., et al. "Role Of A Natriuretic Factor In Essential Hypertension Hypothesis." *Ann of Inter Med.* 1983;98:785–792.

However, experiments directed to determining the vasoconstrictor effect of endogenous sodium pump inhibitory factors derived from volume-expanded or from hypertensive patients have not been performed to conclusively establish this connection. Nonetheless, it is clear from the foregoing discussion that the experimental evidence presently in existence strongly argues in favor of the existence of endogenous sodium pump inhibitors which are implicated in the mechanism of essential hypertension and other physiopathological processes. See, Shlevin, H. H., "(Na-K-)-ATPase Inhibitors For New Drug Discovery." *Drug Develop Res.* 1984;4:275–284.

These physiopathological processes also include the formation of blood vessels, an important process in both embryonic and postnatal life. A variety of angiogenic factors have been described in the art. See, Auerbach, R., *Angiogenesis-inducing factors: a review.* In: Pick, E., ed. Lymphokinines. Vol. IV. New York: Academic Press; 1981:69–:88. These factors include those produced by normal tissues such as epidermal growth factor and acidic fibroblast growth factor. See, Folkman, J., Angiogenesis:initiation and control. *J. Cell Biol.* 1982;104:212; Furcht, L. T., "Critical factors controlling angiogenesis: cell products cell matrix, and growth factors." *Lab. Invest.* 1986;55:505; Gospodarowidcz, D., Thakral, K. K., "Production of a corpus luteum angiogenic factor responsible for proliferation of capillaries and neovascularization of the corpus luteum". *Proc. Nat'l Acad. Sci.* 1978;75:847; Weiner, H. L., Weiner, L. H., Swain, J. L., "Tissue distribution and developmental expression of the messenger RNA encoding angiogenin". *Science.* 1987;237:280. Angiogenic factors have also been reported in neoplasms of mammals including humans. See, Fett, J. W., Strydom, D. J., Lobb, R. R., et al., "Isolation and characterization of angiogenin and angiogenic protein from human carcinoma cells". *Biochem.* 1985;24:5840 and Weiner, H. L., Weiner, L. H., Swain, J. L., "Tissue distribution and developmental expression of the messenger RNA encoding angiogenin". *Science.* 1987;237:280; Guillino, P. M., "Angiogenesis and oncogenesis". *J. Nat'l Canc. Inst.* 1978;61:639; Kumar, S., West, D., Daniel M., Hancock, A. S., Carr, T., "Human lung tumour cell line adapted to grow in serum-free medium secretes antiogenesis factor". *Int'l J. Canc.* 1983;32:461; Schor, A. M., Schor, S. L., "Tumor antiogensis". *J. Pathol.* 1983;141:385; Shing, Y., Folkman, J., Haudenschild, C., Lund, D., Crum, R., Klsagsbrun, M., "Angiogenesis is stimulated by a tumor-derived endothelial cell growth factor". *J. Cell Biol.* 1985;29:275; Stenzinger, W., Gruggen, J., Macher, E., Sorg., C., "Tumor angiogenic activity (TAA) production in vitro and growth in the nude mouse by human malignant melanoma". *Eur. J. Canc. Clin. Oncol.* 1983;19:649. It is believed that inhibition of angiogenesis may be due to $Na^+$, $K^+$-ATPase inhibition because fibroblast growth factor binding to its specific receptor is dependent upon the $Na^+$ gradient across the cell membrane and more than 70% of $Na^+$ movement across the plasmatic membrane is based upon sodium pump activity.

Accordingly, it is a principle object of the present invention to disclose and claim a substantially pure endogenous $Na^+$, $K^+$-ATPase inhibitory factor. It is a further object of the present invention to provide effective methodologies for isolating and characterizing this endogenous $Na^+$, $K^+$-ATPase inhibitory factor in its substantially pure form. In this manner, the present invention overcomes the inability of the earlier researchers to isolate, purify and identify such compounds.

Moreover, it is an additional object of the present invention to provide a substantially pure $Na^+$, $K^+$-ATPase inhibitory factor which is biologically active at physiological concentrations of potassium. Further, those skilled in the art will appreciate that the biological activity of the inhibitory factor of the present invention functions in a dose responsive manner making it particularly effective as a pharmaceutical compound for use in therapeutic methodologies.

Thus, it is a still further object of the present invention to provide such pharmaceutical compositions and associated methods for their use in treating essential hypertension in mammals as well as for treating cardiac malfunction. Similarly, it is also an object of the present invention to provide pharmaceutical compositions and methods for their use in regulating active sodium transport in mammals as well as functioning as diuretics. It is also an object of the present invention to provide pharmaceutical compositions and methods for their use in inhibiting and/or regulating angiogenesis.

It is also an object of the present invention to clarify the contradictory state of the art with respect to the characterization of endogenous sodium pump inhibitory factors.

SUMMARY OF THE INVENTION

These and other objects are achieved by the composition and methodology of the present invention. Generally stated, the present invention provides a highly purified $Na^+$; $K^+$-ATPase inhibitory factor which is readily identifiable and characterized by specific activities which distinguish it from previously known sodium pump inhibitors.

More specifically, in accordance with the teachings of the present invention, a highly purified $Na^+$, $K^+$-ATPase inhibitory factor is identified which can be extracted from bovine hypothalamic and pituitary tissues. The exemplary extraction and purification steps include methanol and lipid extractions, two lipophilic chromatographies and semi-preparative and analytical reverse phase high pressure liquid chromatography (HPLC). Isolated from both hypothalamic and hypophysis, the highly purified factor is identical in both tissues according to all chromatographic and biological activity criteria.

The pure factor of the present invention has a low molecular weight on the order of less than 1000 Daltons. Further, it is non-peptidic and non-lipidic. What is more, it does not have significant cross-reactivity with anti-digoxin antibody. In the final HPLC purification step of the factor, a pure component single peak is produced. Spectral analysis also identifies a single component throughout the peak having a maximal absorbance at approximately 202–210 nm and at approximately 274–280 nm. Those skilled in the art will appreciate that this absorbance spectrum is markedly distinct from that of previously identified sodium pump inhibiting substances when eluted through the same chromatographic system.

Additionally, the inhibitory activity of the $Na^+$, $K^+$-ATPase inhibitory factor of the present invention parallels the absorbance along the chromatographic peak. At physiological concentrations of potassium (5–25 mM) the inhibitory factor of the present invention inhibits $Na^+$, $K^+$-ATPase in a dose responsive manner. Similarly, at physiological concentrations of potassium, the inhibitory factor of the present invention also inhibits $Rb^+$ uptake from erythrocytes and displaces ouabain from its receptor at the enzyme structure in a dose responsive manner. There is also direct evidence that the inhibitory factor of the present invention specifically inhibits basal as well as stimulated angiogenesis in a dose response manner utilizing standard neovascularization observation methodologies known in the art.

As a verifying control, a similar weight of bovine cerebral cortex was processed as a tissue blank through the same exemplary extraction and purification methodology. This control tissue gave no peak and exhibited no inhibitory activity. Conversely, the inhibitory factor isolated and substantially completely purified from hypothalamus and hypophysis was identical in both tissues. However, the specific activity per weight of tissue was 17 times higher in hypophysis than in hypothalamus.

As will be appreciated by those skilled in the art, the dose responsive biological activities of the inhibitory factor of the present invention occur at physiological concentrations of potassium. Accordingly, the inhibitory factor of the present invention has clear implications as a pharmacological treatment in a variety of physiopathological conditions including essential hypertension, cardiac malfunction, angiogenesis and cation regulation.

The above discussed and many other features and attendant advantages of the present invention will become apparent to those skilled in the art from a consideration of the following detailed description. Reference will be made to the appended figures which will now be first described briefly.

BRIEF DESCRIPTION OF THE DRAWINGS

FIG. 2A1 presents the chromatogram analysis of FIG. 1A further illustrating the localization of the inhibitory activity.

FIG. 2A2 details the automatic overlay spectra form 310 nm to 210 nm corresponding to the profile of FIG. 1A further illustrating the localization of the inhibitory activity.

FIG. 2B1 presents the chromatogram analysis of FIG. 1B further illustrating the localization of the inhibitory activity.

FIG. 2B2 details the automatic overlay spectra from 310 nm to 210 nm corresponding to the profile of FIG. 1B further illustrating the localization of the inhibitory activity.

DETAILED DESCRIPTION OF THE INVENTION

In a broad aspect, the present invention is directed to a highly purified, low molecular weight, non-peptidic, non-lipidic, non-digoxin-like Na+, K+-ATPase inhibitory factor, its identification, characterization and use. As noted above, considerable effort has been devoted by numerous researchers to identify and characterize endogenous inhibitors of Na+, K+-ATPase with significant resulting controversy about the chemical structure and mechanisms of action of such compounds. It is believed that a primary reason for this controversy is due to the use of partially purified preparations by the prior art researchers. Thus, attempts to isolate an inhibitor from tissue and fluids have been unsuccessful because of artifactual interferences caused by such mixtures of nonspecific substances.

In accordance with the teachings of the present invention, to overcome such problems, three strategies were adopted: the first involved a multiple assay protocol to overcome the differing interferences of each assay; second, appropriate tissue controls were utilized in the purification steps; and third, known endogenous inhibitory substances which did not fulfill all of the criteria for a Na+, K+-ATPase inhibitor were identified during the purification process to confirm that the purified factor was a previously unknown substance.

Because the mid-brain has been implicated in the control of circulating Na+, K+-ATPase inhibitors, hypothalamus and pituitary tissues, specifically bovine hypothalamus and hypophysis, were selected as exemplary sources for the inhibitory factor disclosed in the present invention. However, it will be appreciated by those skilled in the art that the present invention is not limited to inhibitory factors extracted from bovine hypothalamic and pituitary tissues. Rather, other source tissues and fluids such as placenta and urine may also be processed in accordance with the teachings of the present invention. Moreover, the specific Na+, K+-ATPase inhibitory factor disclosed and claimed herein may also be produced artificially or through recombinant DNA technology or the like. Accordingly, the present invention is not limited by specific source tissues.

Nonetheless, because of the relatively high concentrations of desired inhibitory factor found in bovine hypothalamic and hypophysary tissues, the preferred exemplary embodiment of the present invention will be discussed in the context of these source tissues. Additionally, for the purpose of this application the desired Na+, K+-ATPase inhibitory factor will also be referred to as, "hypothalamic hypophysary inhibitory factor" (HHIF) for simplicity.

Utilizing bovine hypothalamus and hypophysis as source tissue, the preferred extraction procedure includes a homogenization step in methanol, LH-20 lipophilic chromatography and purification steps utilizing HPLC techniques. As will be appreciated by those skilled in the art, the complete purification of HHIF is difficult because the assay systems utilized are prone to interference by a number of artifacts.

The present invention overcomes these difficulties through the use of the previously-mentioned multiple bio-assay strategy for the detection of HHIF. This multi-assay strategy eliminates false positive results because each assay is prone to interference by differing substances and the multiple assays therefore cancel out these artifacts. Additionally, parallel purification of bovine cerebral cortex utilized as a control also eliminates nonspecific substances. Similarly, interference by known endogenous inhibitory factors was eliminated by identifying such compounds and their derivatives during the purification process to confirm that HHIF was a previously unknown substance.

More specifically, the exemplary purification protocol of the present invention initially utilized seven different bio-assays: a direct $P^{32}$ and an indirect coupled ATPase assay; $^{86}$RB+uptake assay; ouabain binding displacement assay; SCC toad bladder assay; a solid phase digoxin radio immunoassay; and a digoxin radio immunoassay based upon charcoal separation. The SCC bladder assay was subsequently abandoned after the initial steps of the purification were established. Additionally, the digoxin assays need only be utilized as detectors of immunoreactive substances because, in accordance with the teachings of the present invention, HHIF loses its reactivity with anti-digoxin antibodies in the highly purified state disclosed and claimed, while maintaining all other identifying characteristics.

It should also be noted that the use of suitable controls initially is important to the purification process; particularly where the bioassays utilized are not totally specific. In the method of the present invention every purification step initially utilized a corresponding tissue control as well as reagent blanks. Tissue controls utilized include bovine skeletal muscle and bovine cortex.

To eliminate misleading results during the purification process produced by other endogenous inhibitory substances, the exemplary method of the present invention utilized a diode array detector in the HPLC apparatus in conjunction with appropriate software. The software contained a library of known compounds and their derivatives with their characteristic UV absorption spectra and retention times in the different chromatographic conditions used. This library included such known endogenous inhibitory substances as unsaturated fatty acids, lysophosphatadylcholines, dihydroxyeicosatrinoic acid, dehydroepiandrosterone sulfate, lignan, dopamine, and ascorbic acid. This detector made it possible to identify known inhibitory substances during the purification process. This greatly simplified distinguishing HHIF from such previously known compounds. However, while the diode array detector utilized in the present invention is preferred, it should be appreciated that additional methods and apparatus for distinguishing known inhibitory compounds are also contemplated as being within the scope of the present invention.

The following materials and methods were utilized to extract, purify and characterize the $Na^+$, $K^+$-ATPase inhibitory factor of the present invention.

Chemicals. Phosphoenolpyruvate, ATP, ouabain, digoxin and phospholipase C were purchased from Sigma Chemical Co., NADH from Boehringer Mannheim and the enzymes pyruvate-kinase and lactate dehydrogenase from Merck (Darmstadt). The radioactive materials were all purchased from Amersham Int. (England). Organic solvents were of high performance liquid chromatography (HPLC) grade. Other chemicals were of analytical grade.

Tissue Extraction. The exemplary method used was a modification of the one described by Carilli et al. "Hypothalamic Factor Inhibits the (Na/K)ATPase From the tracellular Surface." *J Biol Chem.* 1985;260,No.2:10-27-1031. One Kg. of frozen tissue (bovine hypothalamus, hypophysis, cerebral cortex) is homogenized in 1 L Methanol 100% and stirred overnight at 4° C. The solution is suction-filtered through Whatman No. 54 paper and the residue resuspended in 2 L Methanol:Water (4:1,v:v), restirred overnight and refiltered. The filtrates are pooled, evaporated in vacuum at 40° C. and resuspended in 1 L of water. The aqueous phase lipid extracted with ⅓ vol.Petroleum ether x3 and ⅓ vol.-Chloroform x3. The control tissues were extracted with the same procedure.

$^3$H-ouabain binding displacement. The method described by Brooker and Jelliffe "Serum Cardiac Glycoside Assay Based Upon Displacement of 3 H-Ouabain from Na-K-ATPase." *Circulation.* 1972;XLV:20-36 was used with light variation. Inhibitor samples and purified enzyme were preincubated in a total volume of 1 ml with the following final concentrations: 0.2 M Tris-ClH,100 mM NaCl, 0.25 mM EDTA, 5mM MgCl$_2$, 5 mM ATP and 50 nCi of $^3$H ouabain (20,6 Ci/mmol) at 37° C., pH 7.4. Incubation was stopped by placing the tubes in ice and bound $^3$H ouabain was trapped by filtering through cellulose nitrate disks of 0.22 μm pore size (Millipore, USA), dried out and counted by liquid scintillation. Blanks to discount non-specific binding were obtained by adding 1 mM cold ouabain to the assay. Percentage of ouabain displacement was calculated by comparing inhibitor samples to control tubes without inhibitor.

Radioimmunoassay. Generally, a digoxin antibody covalently bound to the inner surface of polypropylene tubes was used, obtained from Immunochem (USA). Digoxin standards and samples were diluted 1:2 in 1.5M Tris-ClH, pH 7.5. $^{125}$I-digoxin (2000 μCi/μg) was used.

As stated previously, this cross reaction is not a necessary criteria for HHIF. However, this method is used to follow and evaluate digoxin-like substances in the exemplary purification procedures. An RIA commercial kit was used, purchased from Immunochem. Digoxin standards and sample preparations were diluted 1:2 in 1.5M Tris-ClH, pH 7.5. Digoxin antibodies were covalently bound to the inner surface of polypropylene tubes. After a 30 min. incubation at 20° C., tubes with sample plus $I^{125}$-digoxin unbound radioactivity are discarded and the tubes counted by liquid scintillation. Values of DLA are calculated by extrapolating from the standard curve constructed on semilogarithmic paper with plots of B/B. vs. concentration.

A radioimmunoassay method based on charcoal separation using a commercial antibody elicited in rabbit against digoxin is also used as described by Smith, T. W., et al. "Determination Of Therapeutic And Toxic Serum Digoxin Concentrations By Radioimmunoassay." *The New England J Med.* 1969;1212-1216.

$Na^+$, $K^+$-ATPase Activity. The enzyme was purified from porcine kidney outer medulla by the procedure of Jorgensen. Jorgensen PL, "Purification and characterization of (Na,K) ATPase." *Biochim Biophys Acta* 1974; 356:36-52. ATPase activity was 98% ouabain sensitive and showed a specific activity of 10 μmol/mg prot./min. Unless stated otherwise the standard $Na^+$, $K^+$-ATPase inhibition assay used was performed as described by Josephson, et al. with some variations. Josephson L, et al. "Isolation of a potent (Na+-K+)ATPase Inhibitor From Striated Muscle." *Biochemistry* 1977; 16:4572-4578.

Final assay volume (1 ml) concentrations were as follows (mM): NaC1,100;KCl,25;phosphoenolpyruvate,1.4; MgCl$_2$,6; DTT,1; HEPES-TEA,20; disodium ATP,3; NADH,0.26; pyruvate kinase,10 μg/ml; and lactatodehydrogenase, 10 μg/ml. HHIF samples were previously preincubated with purified enzyme in 1M Tris-ClH,pH 7.4, containing 6 mM MgCl$_2$, at 37° C. during 2 h. When ouabain was compared with HHIF for inhibition of $Na^+$, $K^+$-ATPase the final $K^+$ concentration in the assay medium was reduced to 5 mM and preincubated 30 min. One unit (U) of inhibitory activity was defined as the amount of HHIF required to inhibit 8 μg of purified (Na/K)ATPase by 50% in the standard assay conditions. Simultaneously with the initial purification steps, an ATP-P$^{32}$ assay was used as described below.

Lipophylic Chromatography. Supernatant from the foregoing tissue extraction was loaded onto a Sephadex LH-20 column, 315×85 cm equilibrated and eluted with 100% Ethanol. Active inhibitory fractions eluting just ahead of the salt peak were pooled and concentrated by successively smaller LH-20 columns including intermediate lipid reextractions.

HPLC Semipreparative. A C$_{18}$ μBondapak column (7.8×300 mm.) of 10 μm of particle size was used. Mobil phase was an increasing linear gradient, from 0-100%, of acetonitrile:water in 0.1% TFA over 260 min. at a flow rate of 1 ml/min. Sample loaded ranged from 120-180 U. Recording wave length used was 214 mm.

HPLC Analytical. Initially, three separate runs were made: (A) A $C_{18}$ Novapak column (3.9×150) of 4 μm particle size was used. Mobil phase was an increasing linear gradient, from 0-50%, of acetonitrile:water in 0.1% TFA over 260 min. at a flow rate of 0.5 ml/min. Sample loaded ranged from 30-120 U. (B) A $C_{18}$ μBondapak column of 4 μm particle size was used. Mobil phase was an increasing linear gradient, from 30-80% of acetonitrile:water in 0.1% TFA over 220 min. at a flow rate of 0.5 ml/min. Sample loaded ranged from 30-120 U. (C) A $C_{18}$ μBondapak column of 4 μm particle size was used. Mobil phase was a step gradient of 0-40% during 60 min., 40-80% during 120 min. and 80-100% during 60 min. of acetonitrile:water in 0.1% TFA at a flow rate of 0.5 ml/min. Sample loaded ranged from 30-120 U. A Waters 600 E system controller with an IBM computer and a Waters 990 photodiode array detector was used. Subsequently an alternative methodology was developed eliminating the $C_{18}$ Nova-Pak primary chromatographic analysis. This alternative methodology requires only two separate HPLC runs and reduces any complications that may result from the undesirable binding of the inhibitory factor to the column.

Physical-Chemical Treatment. For the acid treatment the conditions for amino acid analysis of peptides were employed. 2-20 U doses of HHIF were incubated with 5.7 M HCL-0.005% Mercaptoethanol at 115° C. for 21 h under vacuum. The remaining HCl was removed by lyophilization and the sample was assayed for inhibition of $Na^+$, $K^+$-ATPase. For the alkaline treatment a dose of 2 U of HHIF was incubated with 0.2 N NaOH at 27° C. for 2 h, the samples were lyophilized and neutralized with buffer Tris-HCl pH 5.0 and assayed as described above. Charring was carried out at 250° C. for 2 h. In all cases the appropriate reagent controls were also included in the inhibition assay.

Protein Incubations. 2 U of HHIF were incubated for 2 H at 37° C. with 6 μgr of phospholipase C or 10 μgr of BAS in 1 M Tris-HCl, pH 7.4. The incubations were stopped by heating the samples at 80° C. for 10 min. and centrifugation at 16,000 g for 5 min. and the supernatants were assayed for inhibition of $Na^+$, $K^+$-ATPase.

Direct $ATP^{32}$ Enzyme Assay. The simultaneous study of inhibition by two assays is preferred because some interferences affect the coupled reaction of the previously mentioned $Na^+,K^+$-ATPase inhibition assay while others interfere in the direct measurement of liberated $P^{32}$. More specifically, some chromogenic substances make NADH absorbance recording rather difficult. Similarly, compounds such as bivalent cation metals ($Cu^{2+}$ or $Zn^{2+}$) may inhibit the other enzymes of the coupled assay, lactate dehydrogenase and pyruvate kinase. The ATP-$P^{32}$ assay involves incubation of the endogenous inhibitor and the ATPase purified from pig renal medulla, in a medium containing 100 mM NaCl, 50 mM Tris-Cl, ph 7.4, 0.25 mM $Na_2$EDTA, 5 mM ATP, 20 mM KCl and 0.3 μCi of $P^{32}$-ATP. The mixture was incubated for 30 min. at 37° C. and the reaction stopped by adding ice-cold 4% (w/w) charcoal (Norit A) in 0.1 M HCl., 1 mM $NaH_2PO_4$, and $Na_4P_2O_7$. Then the samples were centrifuged at 2000 g for 10 min. and the $P^{32}$ released was determined by liquid scintillation counting.

$^{86}Rb+$ Uptake Assay. Fresh human red blood cells were washed and suspended to 50% cells in Ringer's-glucose (145 mM NaCl, 5 mM KCl, 1 mM CaCl, 1 mM $MgSO_4$, 5 mM $Na_2HPO_4$, 11 mM glucose, pH 7.4. Cells were incubated with or without inhibitor (10 units/150 ul of suspension), at 37° C. for 1 h. (10 units of inhibitor in 50 μl of water were evaporated to dryness in an Eppendorf tube; then 150 μl of 50% red cell suspension was added.) Ouabain (0.2 mM) was added to samples where indicated. Transport was initiated by addition of $^{86}Rb+$(4 μCi/ml). Cells were separated from medium at intervals by layering 40 μl aliquots of the suspension on oil (0.3 ml of dinonylphtalate/silicone (1:1) with 0.8 ml of ice-cold Ringer's-glucose layered over) and spinning for 30 s. in an Eppendorf Microfuge. The tubes were frozen in dry ice/ethanol and the tops were sliced off with a razor blade and mixed vigorously with 0.3 ml of 1% SDS to solubilize the pellet. 4 ml of scintillation liquid was added and the samples were counted for $^{86}Rb+$ content.

In accordance with the foregoing, an exemplary embodiment of the non-digoxin-like $Na^+$, $K^+$-ATPase inhibitory factor of the present invention was prepared as follows:

A crude extract was prepared from one Kg. each of bovine hypothalamus, hypophysis and cerebral cortex as described under materials and Methods. The extract equivalent to 250 gr. of tissue was chromatographed in a Sephadex LH-20 column. The active fractions were concentrated by successive smaller LH-20 columns. At this stage of purification all three tissues showed activity in all the assays, including digoxin immunoreactivity. The specific activity at this stage of purification was 1.5 U/gr. tissue for hypothalamus, 3.4. U/gr. tissue for hypophysis.

The material was further purified in a semipreparative $C_{18}$ Bondapak column as described above. The inhibitory area selected in the hypothalamic and hypophysary profiles from this column for further purification showed no digoxin immunoreactivity. The profile of brain cortex showed inhibitory activity in the void volume. From this stage on, the area in the brain cortex profile corresponding to the selected inhibitory area from the other two tissues, was submitted to the same purification steps as the active area in hypothalamus and hypophysis, and used as control.

The next purification steps included a $C_{18}$ Novapak and a $C_{18}$ Bondapak run in the analytical conditions described above. In each column, the sample injected ranged from 100 to 120 arbitrary units. In the case of brain cortex, where no activity was detected, the amount injected corresponded to the equivalent fraction of hypothalamus injected in each step. The final purification was obtained by an additional chromatography on a $C_{18}$ μBondpak column with the conditions described above. Those skilled in the art will appreciate that the alternative methodology eliminating the $C_{18}$ Novapak run may also be utilized.

Figure 1A:
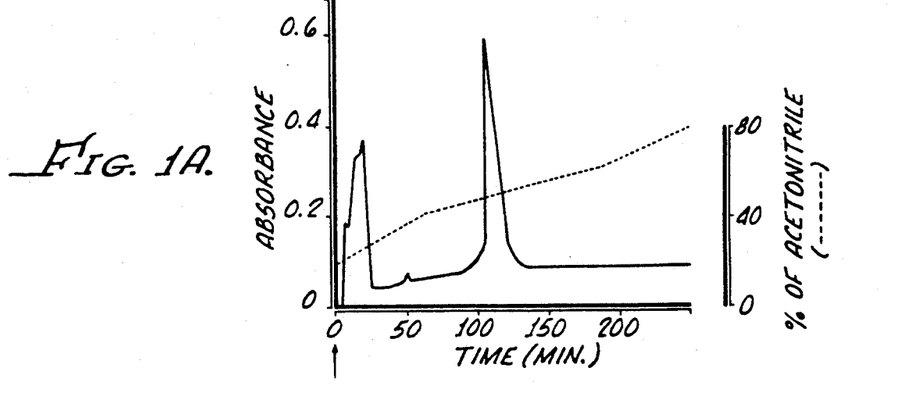
FIG. 1A presents the elution profile of the final HPLC purification of the Na+, K+-ATPass inhibitory factor obtained from a sample of bovine hypothalamus.
Figure 1B:
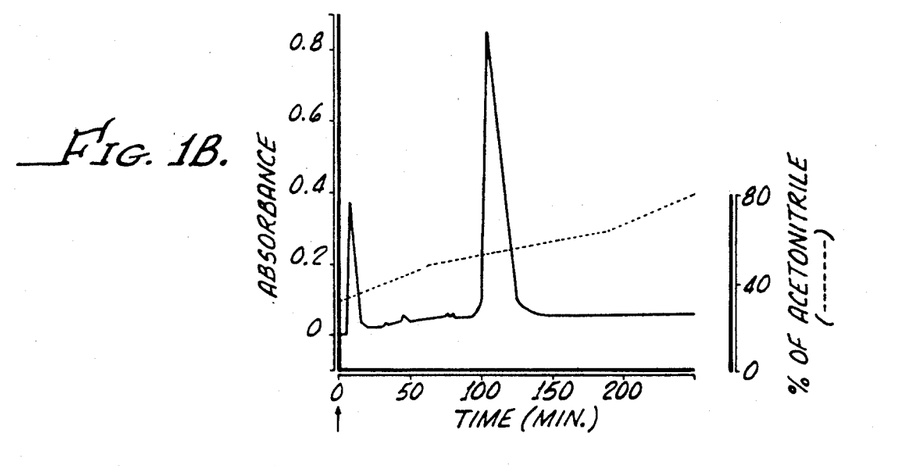
FIG. 1B presents a comparative elution profile to that of FIG. 1A illustrating the final HPLC purification of Na+, K+-ATPase inhibitory factor obtained from bovine hypophysis.
Figure 1C:
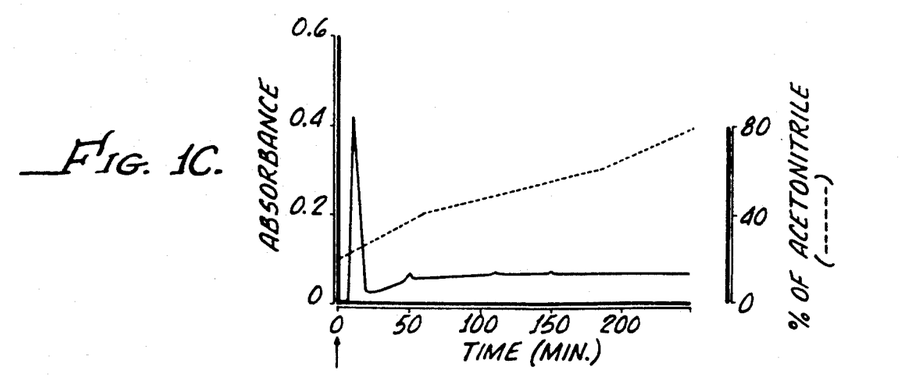
FIG. 1C presents a comparative elution profile to that of FIGS. 1A and 1B illustrating the final HPLC purification of Na+, K+-ATPase inhibitory factor obtained from bovine hypophysis.
Figure 2A:
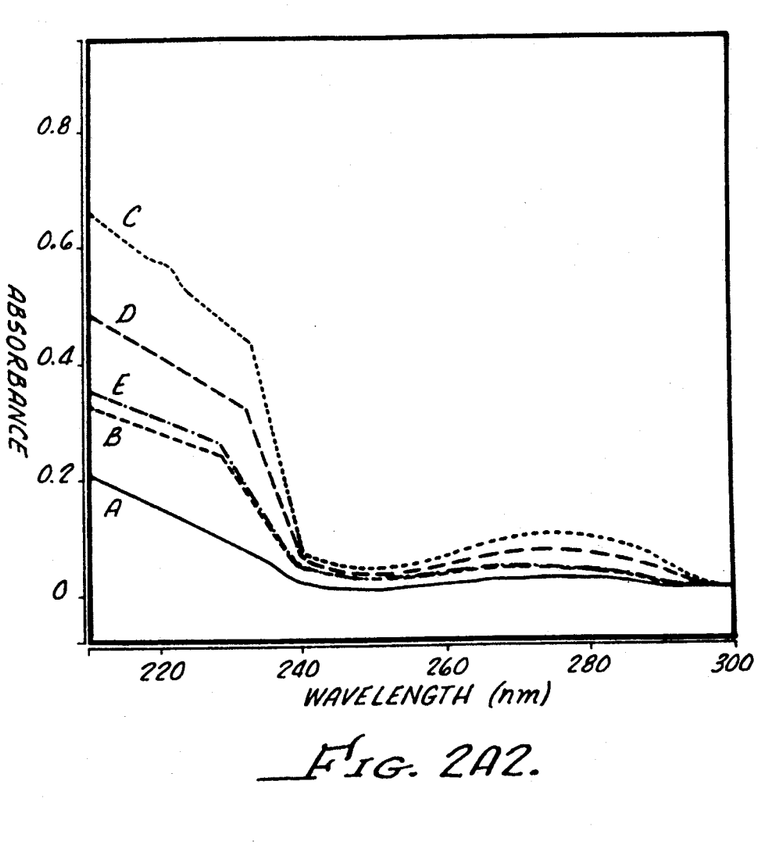
Figure 2A:
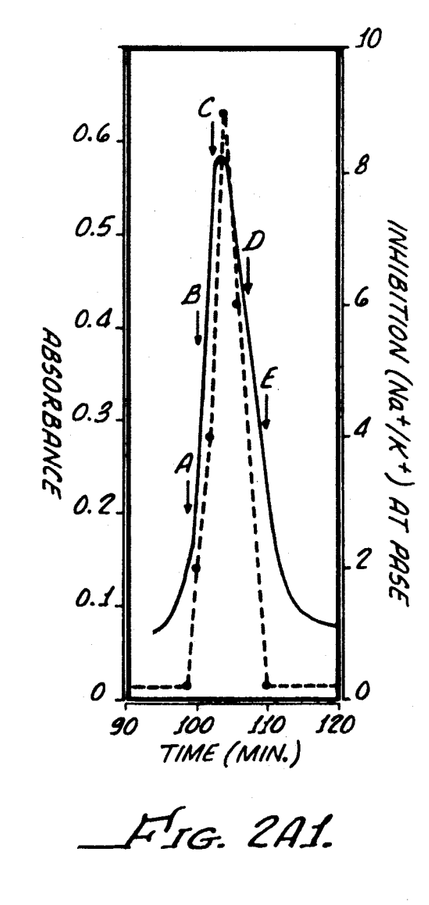
Figure 2B:
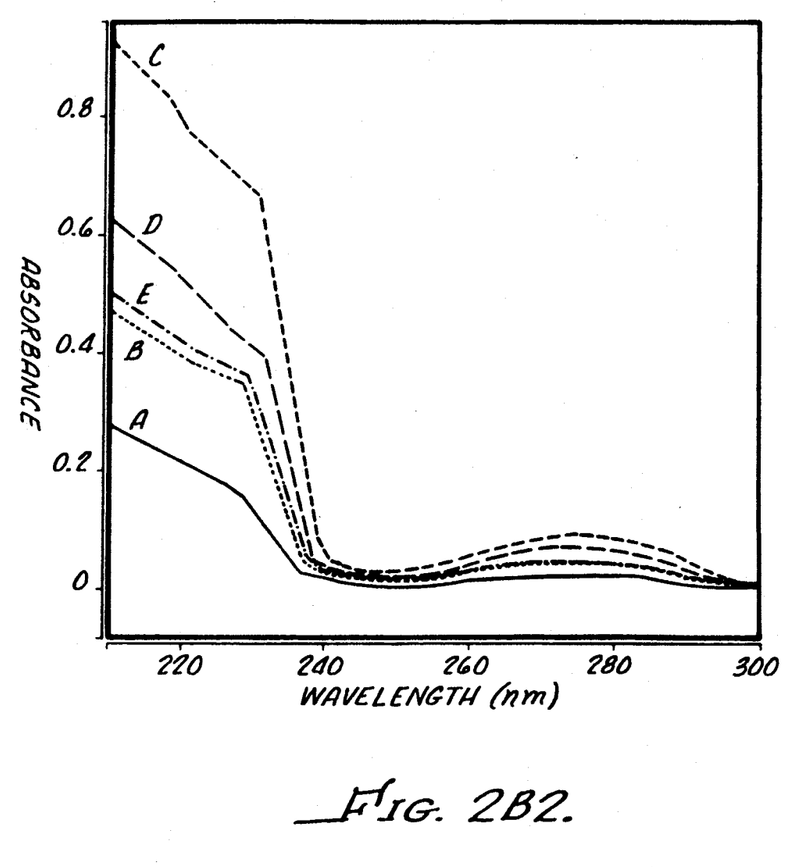
Figure 2B:
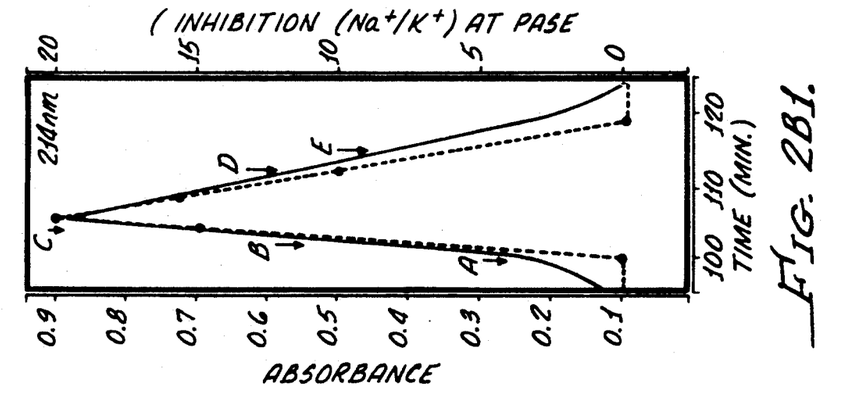
Figure 3A:
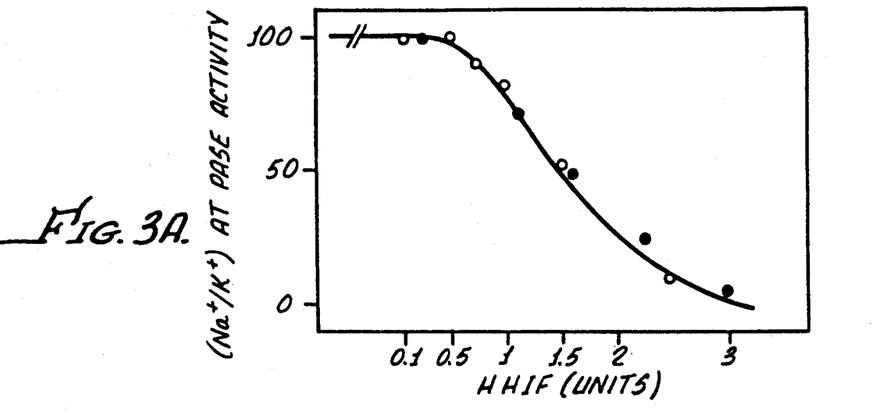
FIG. 3A presents the inhibitory effect of purified hypothalamic (O) and hypophysary factor on Na+, K+-ATPase activity.
Figure 3B:
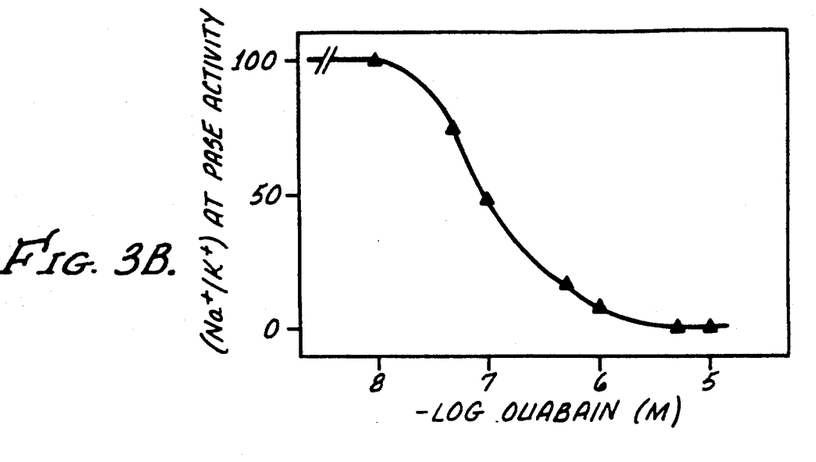
FIG. 3B presents the dose responsive curves of these activities in comparison with ouabain.
Figure 3C:
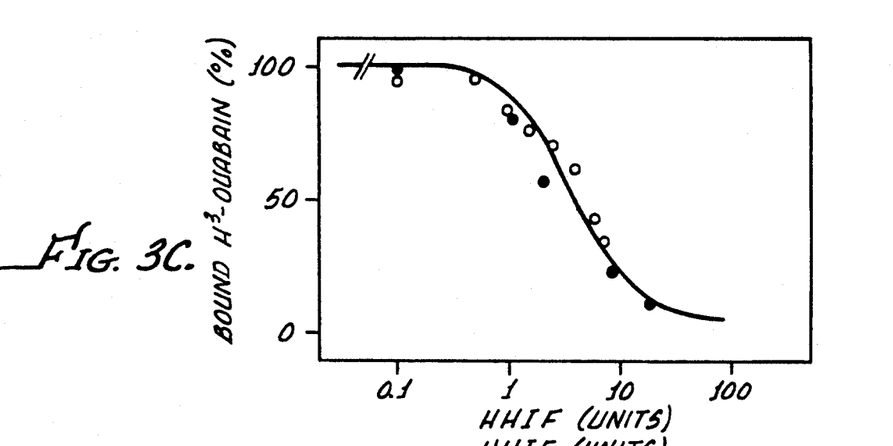
FIG. 3C presents the inhibitory effect of purified hypothalamic (O) and hypophysary factor on binding of $^3$H ouabain to Na+, K+-ATPase.
Figure 3D:
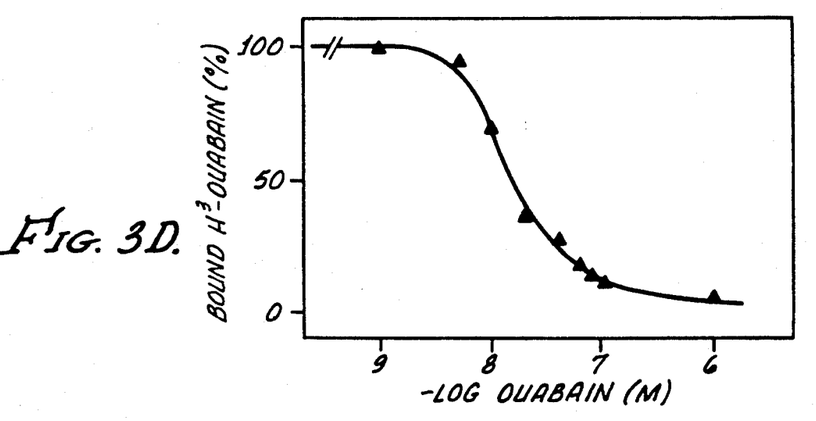
FIG. 3D presents the dose responsive curves of these activities in comparison with ouabain.
Figure 3E:
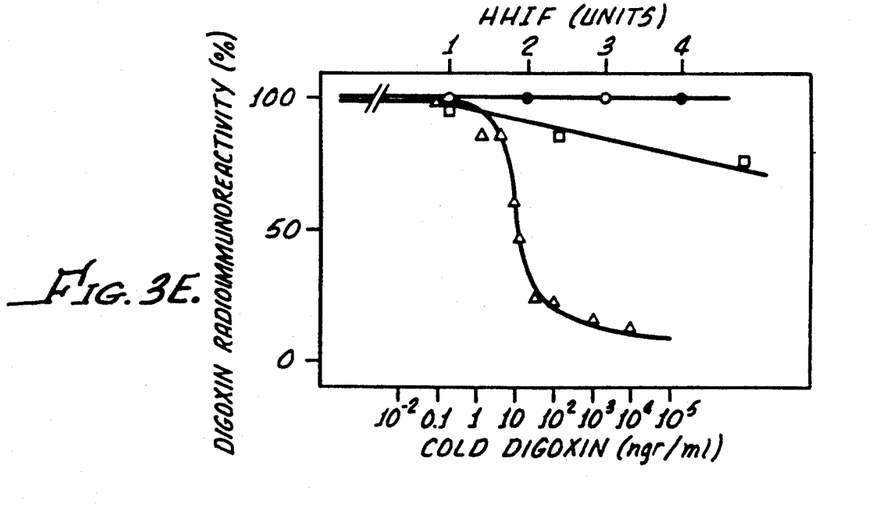
FIG. 3E presents the dose responsive curves of these activities in comparison with digoxin.
Figure 3F:
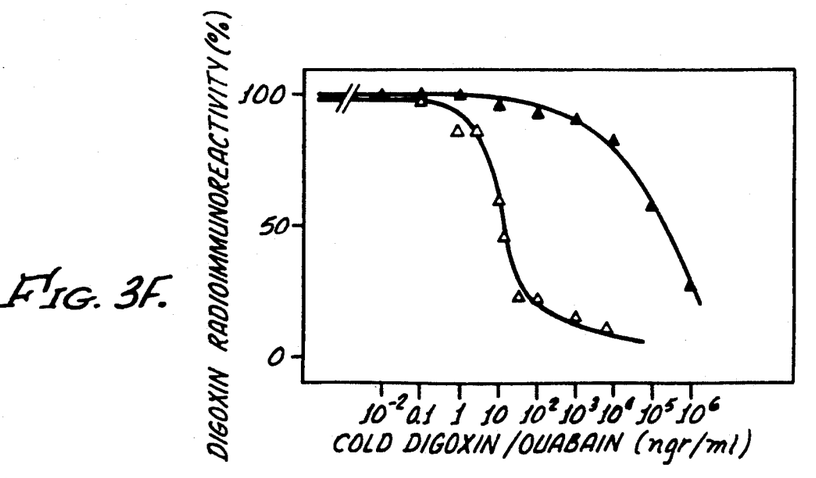
FIG. 3F presents the dose responsive curves of these activities in comparison with digoxin.

FIG. 1 generally represents the elution profiles of the three tissue samples so treated. The active material eluted as a single peak, with similar retention times in both hypothalamus and hypophysis. In the corresponding profile of cortex, no peak nor inhibitory activity was detected. More specifically, FIG. 1 shows comparative elution profiles of the final HHIF purification by HPLC on an FFA $C_{18}$μBondapak column of 4 μm of particle size. The Mobil phase was a step gradient of 0-40% during 60 min., 40-80% during 120 min. and 80-100% during 60 min. of acetonitrile:water in 0.1% TFA at a flow rate of 0.5 ml/min. The samples injected each corresponded to an initial weight of tissue of hypothalamus 350 gr. (A), hypophysis 42 gr. (B), brain cortex 350 gr. (C). The arrows indicate the time of sample injection. Two minute fractions, except for the peak area which was manually done, were collected and monitored for $Na^+$, $K^+$-ATPase inhibitory activity. Only in the peaks that eluted at 108 min. in the profiles of A and B was inhibitory activity detected.

FIG. 2 generally shows the localization of the inhibitory activity in the peaks corresponding to hypothalamus (above) and hypophysis (below) of the profiles of FIG. 1, A and B. In each peak, the automatic multichromatogram analysis of the absorbance of each peak at 212, 230 and 274 nm (not shown) shows coincidence in the peak maxima as an index of homogeneity. The inhibitory activity determined in the standard assay superimposes the absorbance in both peaks. In FIG. 2 the chromatogram profiles are presented showing the localization of the inhibitory activity (●) in the peaks corresponding to hypothalamus (above) and hypophysis (below). Automatic overlay spectra acquired from the right slope (a, b) peak maxima (c) and left slope (d, e) from 210 nm to 210 nm in the peaks corresponding to hypothalamus (above) and hypophysis (below) are detailed in graphs A2 and B on the right of FIG. 2.

The total inhibitory activity of the peaks is of 50 U for hypothalamus corresponding to 350 gr of original tissue and of 105 U for hypophysis corresponding to 42 gr of original tissue. In FIGS. 1 and 2 the spectral analysis, in both peaks, showed a single component throughout the peak. With an autogain, all the spectra along each peak and between both peaks were superimposed (not shown) with two maximums of absorbance at 202 and 274.

The apparent molecular mass of HHIF was determined from ultrafiltration studies to be on the order of less than 1000 Daltons. The quantities of HHIF recovered from hypophysis and hypothalamus were not measurable by a microbalance (Cahn 4700, Cerritos, Calif.; reproducible lower limit, 10μ; readable lower limit, 1 μg) because the amounts recovered were too small.

Charring at 250° for 2 h destroyed the activity of HHIF. Similarly, alkaline hydrolysis for 2 h destroyed 70% of the activity. Conversely, the activity was not affected by acid hydrolysis or by phospholipase C digestion.

Incubation of HHIF with BSA did not affect the inhibitory activity suggesting that this factor is not lipidic. To further test this possibility, the lipidic extraction residue (Chloroform and Petroleum Ether residues) obtained from 1 Kg of hypothalamic tissue was processed through the purification protocol in the same fashion as the earlier tissue samples. No inhibitory activity nor characteristic peak in the final purification was obtained from the lipidic extraction.

Additionally, 20 U of purified HHIF obtained from hypothalamus was submitted to acid hydrolysis and amino acid analysis with a negative result. The amount of factor analyzed gave an O.D. at 274 nm similar to that of 20 μM of a 500 Dalton peptide with tyrosine residues.

The purified HHIF obtained from hypothalamus and hypophysis were also compared with ouabain for inhibition of $Na^+$, $K^+$-ATPase, $^3H$ ouabain binding to the enzyme and digoxin binding to anti-digoxin antibody (FIG. 3). The graphs of FIG. 3 detail the inhibitory effect of purified hypothalamic (O) and hypophysary (●) factor on $Na^+$, $K^+$-ATPase activity (A), on binding of $^3H$ ouabain to $Na^+$, $K^+$-ATPase (C) and cross-reactivity with anti-digoxin antibody (E). The dose responsive curves of these activities were determined in comparison with ouabain (▲)(B, D, F) and digoxin (△)(E, F) under the same assay conditions. Each point is the mean of duplicate determinations in two separate experiments and in A to D using two different preparations of $Na^+$, $K^+$-ATPase and expressed as the percentage of maximum $Na^+$, $K^+$-ATPase activity, maximal binding of $^3H$ ouabain to $Na^+$, $K^+$-ATPase, and maximal binding of $^{125}I$ digoxin to anti-digoxin antibody. In E the cross-reactivity of partially purified hypothalamic factor (□) is also represented.

For these studies the same definition of unit was used, namely the amount necessary to inhibit 50% $Na^+$, $K^+$-ATPase activity in the standard assay (25 mM $K^+$ and 2 h incubation).

In FIG. 3 the biological activity of the factor purified from both tissues was superimposed in the dose response curves. HHIF paralleled the ouabain displacement curve obtained with ouabain but the slope of the dose-response curves of inhibition were different. The purified HHIF did not cross-react with the anti-digoxin antibody at the doses tested while ouabain weakly cross-reacted. Partially purified hypothalamic factor, obtained after the lipophilic chromatography did show cross-reactivity with this antibody.

Additionally, to further distinguish the HHIF of the present invention from known inhibitory compounds, a variety of compounds known to inhibit $Na^+$, $K^+$-ATPase were subjected to the same HPLC conditions. These compounds were Arachidonic acid, Linoleic acid, Cholesterol, OH-Progesterone, Androsterone, Epiandrosterone, Testosterone, Phosphatidylcholinedioleyl, Phosphatiletorolamine-dioleyl, Lisophosphatidyletanolenic-deyl, Chlormanidone, Dopamine, 5H-Thyrosine, Glycocholic acid, Glicoquenodeoxycholic acid, Quenodeoxycholic acid, OH-Phenylacetic acid, and OH-Phenylpyruvic acid, OH-Phenyllactic acid, OH-Benzoic acid. When 100 to 200 μg of these compounds were chromatographed as described above, none had a retention time similar to that of HHIF, nor a similar spectra.

From the foregoing, those skilled in the art will appreciate that, in accordance with the teachings of the present invention, pure HHIF has now been isolated and characterized. Moreover, it is now possible to completely purify HHIF thereby obtaining a homogenous peak with a characteristic spectra that has the same slopes and peak maxima. As shown in the exemplary embodiments, a pure peak, with the same characteristics of retention time, homogeneity and characteristic spectra can be obtained with the same purification protocol from both bovine hypothalamus and bovine hypophysis. The $Na^+$, $K^+$-ATPase inhibitory activity coincides in both tissues with the absorbance of pure HHIF. Further identity between the factor purified from both tissues is demonstrated by the overlay in the curves of inhibition of $Na^+$, $K^+$-ATPase and $^3H$ ouabain displacement from the enzyme. Conversely, the control tissue, bovine cerebral cortex, processed throughout the purification procedure gives a final chromatogram superimposed to the base line without any detectable inhibitory activity. Again, it should be re-emphasized that the present invention is not limited to specific source tissues or methodologies for purifying HHIF. Rather, the foregoing methodologies are exemplary of the best mode currently available for identifying and characterizing HHIF and other alternative methodologies and sources are contemplated as being within the scope of the present invention.

The loss of cross-reactivity with anti-digoxin antibodies during the purification procedure indicates the risk of using such characteristic as a marker in purification of similar factors. Further, it clearly indicates that this inhibitory factor cannot be designated "digoxin-like."

Those skilled in the art will appreciate that this hypothalamic hypophysary inhibitory factor (HHIF) is non peptidic judging by ,its resistance to acid hydrolysis and its negative aminoacid analysis. What is more, it has a molecular weight of less than 1000 Daltons as suggested by ultrafiltration experiments, is destroyed by alkaline hydrolysis, and is not lipidic judging by the incubations with BSA and phospholipase and the lipid extraction experiments described. Moreover, its chromatographic characteristics and spectra are different from those of any of the other substances tested or from the other tissue factors already discussed. Thus the compound of the present invention is readily identifiable and clearly distinguished from known prior art compounds.

As will also be appreciated by those skilled in the art, the distinct biological activities of the HHIF produced in accordance with the teachings of the present invention strongly implicate its usage as a medicament for treating a variety of physiological ailments including essential hypertension, cardiac malfunction, inhibition or regulation of angiogenesis, regulation of cation transport and as a diuretic. The compound may be administered orally, or through injection, or by other standard administration routes in an effective amount as determined by clinical trials. Additionally, the compound can be mixed with a pharmaceutically acceptable carrier such as the normal acceptable additives, excipients and the like. Thus, it is also contemplated as being within the scope of the present invention to utilize a therapeutically effective amount of HHIF as a pharmaceutical compound in methods for treating essential hypertension, cardiac malfunction, regulating angiogenesis, and for regulating active sodium transport in mammals.

Having thus described exemplary embodiments of the present invention, it should be noted by those skilled in the art that the written disclosures are exemplary only and that various other alternatives, adaptations, and modifications may be made within the scope of the present invention. For example, HHIF need not be extracted from mammalian tissues and may be produced artificially or through recombinant DNA technologies. Accordingly, the present invention is not limited to the specific embodiments illustrated herein, but is only limited by the following claims.

I claim:

1. A substantially pure non-digoxin-like $Na^+,K^+$-ATPase inhibitory factor wherein said factor:

has a molecular weight of less than 1000 Daltons;

does not substantially cross-react with anti-digoxin antibody;

exhibits maximal UV absorbance at approximately 202–210 nm and at approximately 274–280 nm;

is non-peptidic as determined by its resistance to acid hydrolysis;

is non-lipidic as determined by its resistance to incubation with BSA or phospholipase; and loses substantial activity following alkaline hydrolysis.

2. The $Na^+,K^+$-ATPase inhibitory factor of claim 2 wherein said factor loses substantial activity following charring.

3. The $Na^+,K^+$-ATPase inhibitory factor of claim 1 wherein said factor substantially inhibits the ouabain-sensitive fraction of $Na^+,K^+$-ATPase in a substantially reversible manner at physiological concentrations of potassium.

4. The $N^+,K^+$-ATPase inhibitory factor of claim 1 wherein said factor substantially displaces ouabain from its receptor at the enzyme structure.

5. The $Na^+,K^+$-ATPase inhibitory factor of claim 1 wherein said factor substantially inhibits $Rb^+$ uptake from erythrocytes.

6. A method for treating essential hypertension in a patient suffering therefrom, said method comprising the step of administering a therapeutically effective amount of the inhibitory factor of claim 1 to said patient.

7. A pharmaceutical composition comprising an effective amount of the inhibitory factor of claim 2.

* * * * *

UNITED STATES PATENT AND TRADEMARK OFFICE
CERTIFICATE OF CORRECTION

PATENT NO. : 5,240,714
DATED      : Aug. 31, 1993
INVENTOR(S) : JOSE MARIA SANCHEZ ROF

It is certified that error appears in the above-indentified patent and that said Letters Patent is hereby corrected as shown below:

In column 20, line 24, Claim 2, delete "claim 2" and substitute therefor --claim 1--.

In column 20, line 43, Claim 7, delete "claim 2" and substitute therefor --claim 1--.

Signed and Sealed this

Twenty-sixth Day of April, 1994

Attest:

BRUCE LEHMAN

Attesting Officer          Commissioner of Patents and Trademarks